United States Patent
Lee et al.

(10) Patent No.: US 11,685,809 B2
(45) Date of Patent: Jun. 27, 2023

(54) PHOSPHORUS-CONTAINING POLYMERS, AND METHODS OF PRODUCING THEREOF

(71) Applicant: Novomer, Inc., Rochester, NY (US)

(72) Inventors: Han Lee, Chicago, IL (US); Alexander Tseitlin, Rochester, NY (US); Sadesh H. Sookraj, Rochester, NY (US)

(73) Assignee: Novomer, Inc., Rochester, NY (US)

( * ) Notice: Subject to any disclaimer, the term of this patent is extended or adjusted under 35 U.S.C. 154(b) by 320 days.

(21) Appl. No.: 16/981,437

(22) PCT Filed: Mar. 20, 2019

(86) PCT No.: PCT/US2019/023262
§ 371 (c)(1),
(2) Date: Sep. 16, 2020

(87) PCT Pub. No.: WO2019/183284
PCT Pub. Date: Sep. 26, 2019

(65) Prior Publication Data
US 2021/0009753 A1    Jan. 14, 2021

Related U.S. Application Data (60) Provisional application No. 62/646,806, filed on Mar. 22, 2018.

(51) Int. Cl.
| | |
|---|---|
| *C08G 63/692* | (2006.01) |
| *C08G 63/08* | (2006.01) |
| *C08K 3/30* | (2006.01) |
| *C08K 5/5399* | (2006.01) |

(52) U.S. Cl.
CPC .......... *C08G 63/08* (2013.01); *C08G 63/692* (2013.01); *C08G 63/6922* (2013.01); *C08K 3/30* (2013.01); *C08K 5/5399* (2013.01); *C08K 2003/309* (2013.01); *C08K 2003/3009* (2013.01)

(58) Field of Classification Search
CPC ... C08G 63/08; C08G 63/692; C08G 63/6922
See application file for complete search history.

(56) References Cited

U.S. PATENT DOCUMENTS

| | | | |
|---|---|---|---|
| 2,449,989 A | 9/1948 | Gresham | |
| 2,510,567 A | 6/1950 | Flory | |
| 3,006,963 A | 10/1961 | Bug | |
| 3,033,822 A | 5/1962 | Kibler | |
| 3,732,293 A | 5/1973 | Ackerman | |
| 3,885,155 A | 5/1975 | Anbar | |
| 4,973,841 A | 11/1990 | Purser | |
| 5,438,194 A | 8/1995 | Koudijs et al. | |
| 5,661,299 A | 8/1997 | Purser | |
| 9,187,597 B1 * | 11/2015 | Boday | C08G 63/912 |
| 2002/0106764 A1 * | 8/2002 | Steinbuchel | C08G 75/26 528/289 |
| 2018/0320077 A1 * | 11/2018 | Campbell | C08K 5/02 |

FOREIGN PATENT DOCUMENTS

WO    2009155086 A2    12/2009

OTHER PUBLICATIONS

International Search Report and Written Opinion in International Application No. PCT/US2019/23262 (dated Jul. 23, 2019); 16 pages.
Gresham, T.L. et al. "β-Propiolactone. V. Reaction with Alcohols." Journal of the American Chemical Society, Publication Date: Mar. 1, 1947, 3 pages.
Gresham, T.L. et al. "β-Propiolactone. XIII. Reactions With Sodium Nitrite, Sodium Dithionite, Sodium Cyanide, Sodium Thiocyanate, Sodium Succinimide and Aryl Sulfinic Acids and Their Salts." Journal of the American Chemical Soceity, Mar. 5, 1952. 3 pages.
Iliescu, Smaranda et al. "Polymers containing phosphorus groups and polyethers: from synthesis to application." Chemistry Central Journal 2012, 6:132. 13 pages.
"Sulfur-Containing Polymers." Encyclopedia of Polymer Science and Technology. Sep. 15, 2010. Copyright 2010 John Wiley & Sons, Inc. 67 pages.
Nifantiev, Edward E. et al. "Amides of Trivalent Phosphorus Acids as Phosphorylating Reagents for Proton-Donating Nucleophiles." Chem. Rev., 2000, 100 (10), 3 pages. American Chemical Society.
"Non-diffusing polymeric development accelerators." Author unknown. Research Disclosure, Kenneth Mason Publications, vol. 110, Issue 13, Jun. 1973 (5 pages).
Kawarazaki, Isamu et al., "Synthesis of Unsaturated Nonionic Poly(ester-sulfones) via Acyclic Diene Metathesis (ADMET) Polymerization and Anode-Selective Electrophoretic Deposition." Macromolecular Chemistry and Physics, vol. 217, No. 23, Dec. 1, 2016, pp. 2595-2600 (17 pages).
Winkler, Matthias et al. "Olefin cross-metathesis as a valuable tool for the preparation of renewable polyesters and polyamides from unsaturated fatty acid esters and carbamates." Green chemistry, vol. 16, No. 6, Jan. 1, 2014, p. 3335-3340 (6 pages).
Supplementary Partial European Search Report in co-pending Application No. EP 19 77 1680 dated Nov. 26, 2021 (17 pages).

* cited by examiner

*Primary Examiner* — Robert S Jones, Jr.
(74) *Attorney, Agent, or Firm* — Young Basile Hanlon & MacFarlane, P.C.

(57) ABSTRACT

Provided are methods of producing sulfur- and phosphorus-containing polymers from beta-lactones. The sulfur- and phosphorus-containing polymers include bio-based sulfur- and phosphorus-containing polymers that may be obtained from renewable sources.

5 Claims, 3 Drawing Sheets

PHOSPHORUS-CONTAINING POLYMERS, AND METHODS OF PRODUCING THEREOF

CROSS-REFERENCE TO RELATED APPLICATIONS

This application is a National Stage Filing under 35 USC 371 of the PCT Application No. PCT/US2019/023262 filed Mar. 20, 2019, published as WO2019/183284, which claims priority from U.S. Provisional Application No. 62/646,806 filed Mar. 22, 2018, both of which are incorporated herein by reference in their entirety for all purposes.

FIELD

The present disclosure relates generally to sulfur- and phosphorus-containing polymers, and more specifically to sulfur- and phosphorus-containing polymers that may be produced from beta-lactones.

BACKGROUND

Polymers are generally used in various applications, including textiles, fabrics, automotive applications, carpets, and coatings. Sulfur- and phosphorus-containing polymers may be used, for example, for high elasticity thermoplastic polymers, and fire resistant polymers. Various methods are known in the art to industrially synthesize such polymers. For example, sulfur-containing polymers, such as polyphenylene sulfides, can be synthesized from reaction of sodium sulfide and organic halogen compounds; and phosphorus-containing polymers, such as polyphosphoesters, can be synthesized from ring opening polymerization of phosphonates. See e.g., Encyclopedia of Polymer Science and Technology; and Iliescu et al., Chemistry Central Journal 2012, 6:132.

Alternative methods of producing sulfur- and phosphorus-containing polymers are desired in the art, including methods of producing bio-based sulfur- and phosphorus-containing polymers that can be obtained, either in part or completely, from renewable sources.

BRIEF SUMMARY

Provided herein are methods of producing sulfur- and phosphorus-containing polymers that can be obtained from renewable sources. For example, in some aspects, the sulfur- and phosphorus-containing polymers may be produced from beta-propiolactone, which can be obtained from bio-based ethylene oxide and/or bio-based carbon monoxide.

In some aspects, provided is a method of producing a polymer comprising repeating sulfonyl-dialkanoic acid moieties, or a salt thereof. In some embodiments, the method comprises: combining a beta-lactone with a dithionite compound to produce a sulfonyl-dialkanoic acid; and combining the sulfonyl-dialkanoic acid with a diol compound to produce the polymer by condensation polymerization. In some variations, the beta-lactone combined with the dithionite compound produce a salt of the sulfonyl-dialkanoic acid, and the method further includes neutralizing the salt of the sulfonyl-dialkanoic acid before combining with the diol compound to produce the polymer.

In other aspects, provided is a method of producing a sulfur-containing polymer, the method comprising: combining a beta-lactone with (i) hydrogen sulfide or a salt thereof, or (ii) a thiol compound to produce a sulfur-containing alkanoic acid; and polymerizing the sulfur-containing alkanoic acid to produce the sulfur-containing polymer.

In yet other aspects, provided is a method of producing a phosphorus-containing polyester, the method comprising: combining a beta-lactone with a diol compound to produce an alkanoate compound having two terminal hydroxy groups; and combining the alkanoate compound with a phosphanediamine or phosphanetriamine compound to produce the phosphorus-containing polyester.

In yet other aspects, provided are sulfur- and phosphorus-containing polymers produced according to any of the methods described herein.

DESCRIPTION OF THE FIGURES

The present application can be best understood by reference to the following description taken in conjunction with the accompanying figures, in which like parts may be referred to by like numerals.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are methods to produce sulfur- and phosphorus-containing polymers from beta-lactones. In some aspects, provided are methods of producing sulfur-containing polymers from beta-lactones using dithionite compounds, hydrogen sulfide or a salt thereof, and thiol compounds. In other aspects, provided are methods of producing phosphorus-containing polymers from beta-lactones using phosphanediamine and phosphanetriamine compounds.

Each of these methods is explored in further detail below, along with the sulfur- and phosphorus-containing polymers produced from such methods.

Production of Sulfur-Containing Polymers Using Dithionite Compounds

In some aspects, provided is a method of producing sulfur-containing polymers from beta-lactones and dithionite compounds. When such method is employed, the sulfur-containing polymer comprises repeating sulfonyl-dialkanoic acid moieties. In some embodiments, the method comprises: combining a beta-lactone with a dithionite compound to produce a sulfonyl-dialkanoic acid; and combining the sulfonyl-dialkanoic acid with a diol compound to produce the polymer by condensation polymerization. When the beta-lactone is combined with the dithionite compound, a salt of the sulfonyl-dialkanoic acid may be produced. As such, in some variations, the method further comprises neutralizing the salt of the sulfonyl-dialkanoic acid to produce the sulfonyl-dialkanoic acid, before the condensation polymerization step. For example, the salt of the sulfonyl-dialkanoic acid may be neutralized by an acidic workup.

Figure 1A:
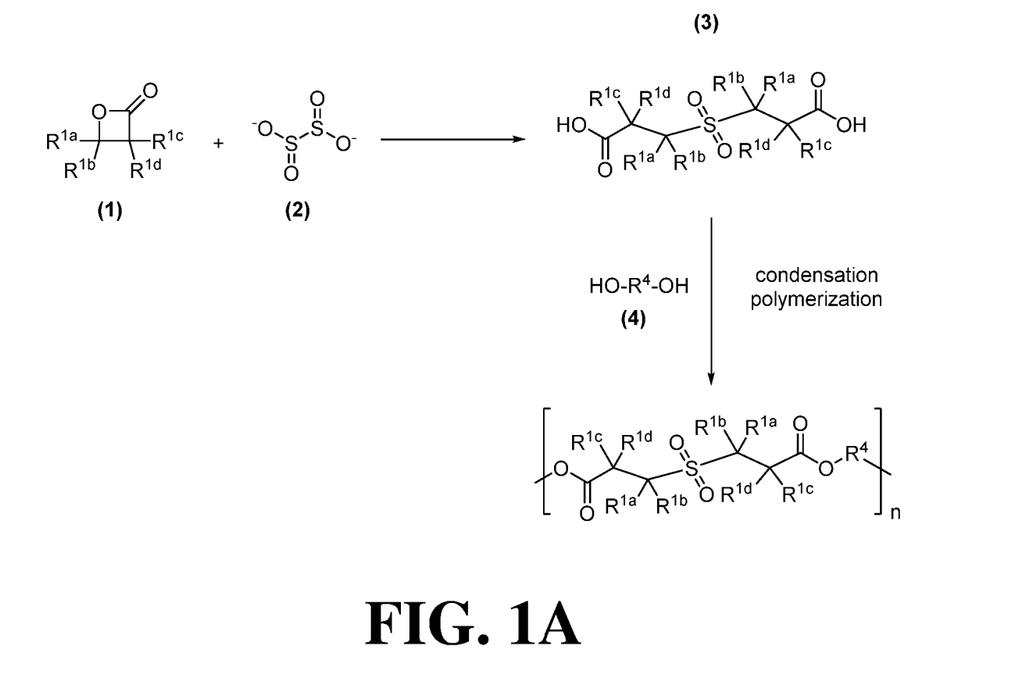
FIGS. 1A and 1B depict exemplary reaction schemes to produce sulfur-containing polymers from beta-lactones using a dithionite compound.

With reference to FIG. 1A, an exemplary method to produce a sulfur-containing polymer comprising repeating sulfonyl-dialkanoic acid moieties is provided. In FIG. 1A, the beta-lactone is a compound of formula (1):

(1)

wherein each $R^{1a}$, $R^{1b}$, $R^{1c}$ and $R^{1d}$ is independently H or alkyl. The compound of formula (1) is combined with a dithionite compound to produce a compound of formula (3):

(3)

wherein $R^{1a}$, $R^{1b}$, $R^{1c}$ and $R^{1d}$ are as defined for formula (1) above.

In some embodiments of the exemplary method depicted in FIG. 1A, the compound of formula (3) may be isolated, and optionally purified, before undergoing condensation polymerization to produce the sulfur-containing polymer. In other embodiments, the compound of formula (3) is neither isolated nor purified before further use.

With reference again to FIG. 1A, the compound of formula (3) is then combined with a diol of formula (4):

(4), wherein $R^4$ is -alkyl-, -cycloalkyl-, -aryl-, -heteroaryl-, -ether-, or -arylalkyl-. The compound of formula (3) and the diol compound are combined under conditions suitable for condensation polymerization to produce the sulfur-containing polymer.

Figure 1B:
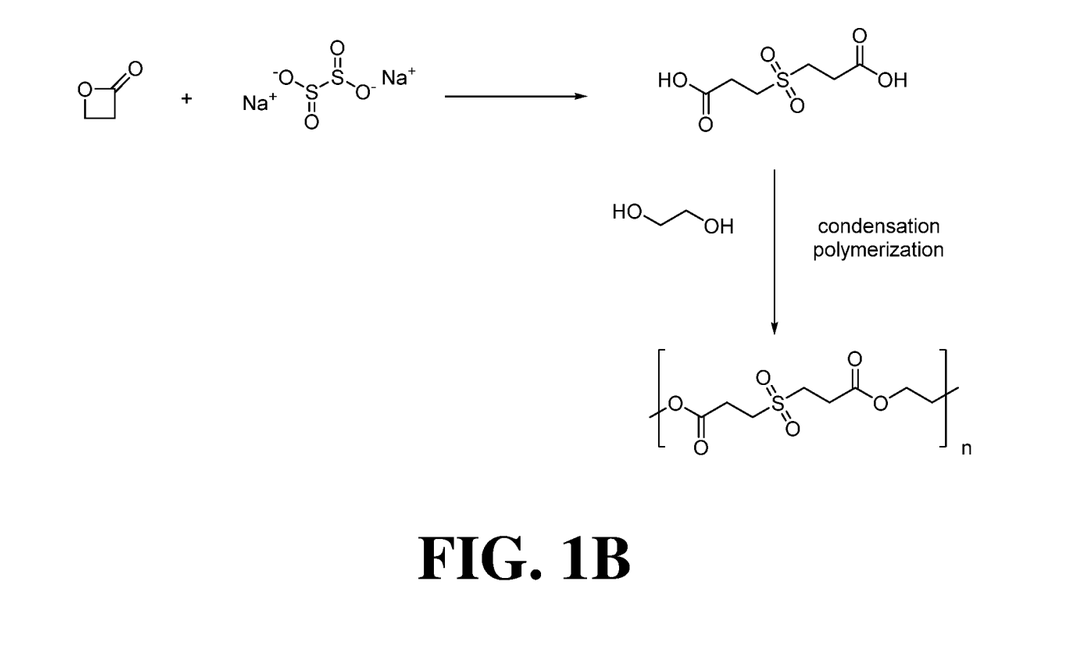

In some variations, the sulfur-containing polymer comprises repeating units of formula:

wherein $R^{1a}$, $R^{1b}$, $R^{1c}$ and $R^{1d}$ are as defined above for formula (3), and $R^4$ is defined above for formula (4). For example, with reference to FIG. 1B, when beta-propiolactone is used, the compound of formula (3) is 3,3'-sulfonyldipropionic acid, which can then be combined with ethylene glycol to produce a polymer comprising repeating units having the structure:

The reagents and products described in the exemplary method in FIG. 1A are described in further detail below.

Compound of Formula (1)

In some embodiments, the compound of formula (1) is wherein each $R^{1a}$, $R^{1b}$, $R^{1c}$ and $R^{1d}$ is independently H or alkyl. In one variation, $R^{1a}$ is H. In other variations, $R^{1a}$ is alkyl. In certain variations, $R^{1a}$ is $C_{1-6}$ alkyl. In another variation, $R^{1a}$ is methyl, ethyl or propyl. In one variation, $R^{1b}$ is H. In other variations, $R^{1b}$ is alkyl. In certain variations, $R^{1b}$ is $C_{1-6}$ alkyl. In another variation, $R^{1b}$ is methyl, ethyl or propyl. In one variation, $R^{1c}$ is H. In other variations, $R^{1c}$ is alkyl. In certain variations, $R^{1c}$ is $C_{1-6}$ alkyl. In another variation, $R^{1c}$ is methyl, ethyl or propyl. In one variation, $R^{1d}$ is H. In other variations, $R^{1d}$ is alkyl. In certain variations, $R^{1d}$ is $C_{1-6}$ alkyl. In another variation, $R^{1d}$ is methyl, ethyl or propyl.

"Alkyl" refers to a monoradical unbranched or branched saturated hydrocarbon chain. In some embodiments, alkyl has 1 to 20 carbon atoms (i.e., $C_{1-20}$ alkyl), 1 to 10 carbon atoms (i.e., $C_{1-10}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), or 1 to 2 carbon atoms (i.e., $C_{1-2}$ alkyl). In certain variations, alkyl groups may include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl.

It should generally be understood that any description of $R^{1a}$, $R^{1b}$, $R^{1c}$ and $R^{1d}$ described herein may be combined the same as if each and every combination were individually listed. For example, in one embodiment, the compound of formula (1) is (also referred to as beta-propiolactone), in which $R^{1a}$, $R^{1b}$, $R^{1c}$ and $R^{1d}$ are all H. In another embodiment, the compound of formula (1) is (also referred to as beta-butyrolactone), in which $R^{1a}$ or $R^{1b}$ is methyl, and the other $R^{1a}$ or $R^{1b}$ is H, and $R^{1c}$ and $R^{1d}$ are also both H. In yet another embodiment, the compound of formula (1) is (also referred to as beta-valerolactone), in which $R^{1a}$ or $R^{1b}$ is ethyl, and the other $R^{1a}$ or $R^{1b}$ is H, and $R^{1c}$ and $R^{1d}$ are also both H.

The beta-lactone, such as the compound of formula (1), may be obtained from any commercially available sources or produced according to any methods known in the art. For example, beta-propiolactone may be obtained by reacting ethylene oxide and carbon monoxide under suitable conditions.

The beta-lactone, such as the compound of formula (1), may be obtained from renewable feedstock. For example, when beta-propiolactone is produced from ethylene oxide and carbon monoxide, either or both the ethylene oxide and carbon monoxide may be obtained from renewable feedstock using methods known in the art. When the beta-lactone, such as the compound of formula (1), is obtained in part or completely from renewable feedstock, the polymer produced according to the methods described herein from such beta-lactone has a biocontent greater than 0%.

Various techniques are known in the art to determine biocontent of a material. For example, in some variations, biocontent of a material may be measured using the ASTM D6866 method, which allows the determination of the biocontent of materials using radiocarbon analysis by accelerator mass spectrometry, liquid scintillation counting, and isotope mass spectrometry. A biocontent result may be derived by assigning 100% equal to 107.5 pMC (percent modern carbon) and 0% equal to 0 pMC. For example, a sample measuring 99 pMC will give an equivalent biocontent result of 93%. In one variation, biocontent may be determined in accordance with ASTM D6866 revision 12 (i.e., ASTM D6866-12). In another variation, biocontent may be determined in accordance with the procedures of Method B of ASTM-D6866-12. Other techniques for assessing the biocontent of materials are described in U.S. Pat. Nos. 3,885,155, 4,427,884, 4,973,841, 5,438,194, and 5,661,299, as well as WO2009/155086.

Dithionite Compounds

As depicted in FIG. 1A, the dithionite compound comprises a moiety of formula (2):

In some variations, the dithionite compound is sodium dithionite or potassium dithionite. A mixture of dithionite compounds may also be used.

The dithionite compound may be obtained from any commercially available sources or produced according to any methods known in the art.

Compound of Formula (3)

In some embodiments, the compound of formula (3) is:

wherein each $R^{1a}$, $R^{1b}$, $R^{1c}$ and $R^{1d}$ is independently H or alkyl. In one variation, $R^{1a}$ is H. In other variations, $R^{1a}$ is alkyl. In certain variations, $R^{1a}$ is $C_{1-6}$ alkyl. In another variation, $R^{1a}$ is methyl, ethyl or propyl. In one variation, $R^{1b}$ is H. In other variations, $R^{1b}$ is alkyl. In certain variations, $R^{1b}$ is $C_{1-6}$ alkyl. In another variation, $R^{1b}$ is methyl, ethyl or propyl. In one variation, $R^{1c}$ is H. In other variations, $R^{1c}$ is alkyl. In certain variations, $R^{1c}$ is $C_{1-6}$ alkyl. In another variation, $R^{1c}$ is methyl, ethyl or propyl. In one variation, $R^{1d}$ is H. In other variations, $R^{1d}$ is alkyl. In certain variations, $R^{1d}$ is $C_{1-6}$ alkyl. In another variation, $R^{1d}$ is methyl, ethyl or propyl.

When the compound of formula (3) is derived from the compound of formula (1), as depicted in FIG. 1A, $R^{1a}$, $R^{1b}$, $R^{1c}$ and $R^{1d}$ are as defined above for formula (1). For example, with reference to FIG. 1B, when the compound of formula (1) is beta-propiolactone, the compound of formula (3) produced is (also referred to as 3,3'-sulfonyldipropionic acid).

Diol Compounds

In some embodiments, the diol compound is a compound of formula (4):

$$HO-R^4-OH \qquad (4),$$

wherein $R^4$ is -alkyl-, -cycloalkyl-, -aryl-, -heteroaryl-, -ether-, or -arylalkyl-. In some variations, $R^4$ is -alkyl-. In certain variations, $R^4$ is $-C_{1-6}$ alkyl-. In one variation, $R^4$ is -methyl-. In another variation, $R^4$ is -ethyl-.

As used generally herein, "-moiety-" refers to the same residues as the moiety described, but having bivalency.

It should be understood that "-alkyl-" refers to the same residues as alkyl, but having bivalency. Examples of -alkyl- include methylene (—CH$_2$—), ethylene (—CH$_2$CH$_2$—), propylene (—CH$_2$CH$_2$CH$_2$—), butylene (—CH$_2$CH$_2$CH$_2$CH$_2$—).

It should be understood that "-cycloalkyl-" refers to the same residues as cycloalkyl, but having bivalency. As used herein, "cycloalkyl" includes a carbocyclic, non-aromatic group that is connected via a ring carbon atom, which contains only C and H when unsubstituted. The cycloalkyl can consist of one ring or multiple rings. In some variations, a cycloalkyl with more than one ring may be linked together by a C—C bond, fused, spiro or bridged, or combinations thereof. Examples of cycloalkyl groups include cyclopropyl, cyclobutyl, cyclopentyl, cyclohexyl, bicyclohexyl, adamantyl, and decahydronaphthalenyl.

It should be understood that "-aryl-" refers to the same residues as aryl, but having bivalency. As used herein, "aryl" refers to an unsaturated aromatic carbocyclic group having a single ring or multiple condensed rings. When there are multiple condensed rings, at least one of the rings is aromatic, but not all rings need to be aromatic. In some variations, an aryl with more than one ring may be linked together by a C—C bond, fused, spiro or bridged, or combinations thereof. Aryl contains only C and H when unsubstituted. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryl may include phenyl and biphenyl.

It should be understood that "-heteroaryl-" refers to the same residues as heteroaryl, but having bivalency. As used herein, "heteroaryl" refers to an unsaturated aromatic carbocyclic group having at least one annular heteroatom, including but not limited to heteroatoms such as nitrogen, oxygen and sulfur. A heteroaryl group may have a single ring or multiple condensed rings. When there are multiple condensed rings, at least one of the rings is aromatic, but not all rings need to be aromatic. In some variations, a heteroaryl with more than one ring may be linked together by a C—C bond, fused, spiro or bridged, or combinations thereof. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. Examples of heteroaryls may include pyridyl, pyridinyl, imidazolyl, thiazolyl, and bipyridyl.

As used herein, "-ether-" refers to bivalent moieties comprising one or more —O— groups. Examples of -ether- may include As used herein, "-arylalkyl-" refers to bivalent moieties comprising an -aryl- group linked to an -alkyl- group. Examples of -arylalkyl- may include Condensation Polymerization Any suitable conditions to convert the compound of formula (3) via condensation polymerization to the sulfur-containing polymer may be employed. For example, in some variations, condensation polymerization is performed at a temperature between 180° C. and 240° C.

In other aspects, provided is a method of producing sulfur-containing polymers, comprising combining a sulfonyl-dialkanoic acid with a diol compound to produce a polymer by condensation polymerization, wherein the polymer comprises repeating sulfonyl-dialkanoic acid moieties. Any of the sulfonyl-dialkanoic acids, including the compound of formula (3), and diol compounds, including the compound of formula (4), described above may be used to produce the sulfur-containing polymers.

Production of Sulfur-Containing Polymers Using Hydrogen Sulfide or Salts Thereof

In some aspects, provided is a method of producing sulfur-containing polymers from beta-lactones and hydrogen sulfide or a salt thereof. In some embodiments, the hydrogen sulfide or a salt thereof is hydrogen sulfide, sodium hydrogen sulfide, or potassium hydrogen sulfide, or any combinations thereof.

In some embodiments, the method comprises: combining a beta-lactone with hydrogen sulfide or a salt thereof to produce a sulfur-containing alkanoic acid; and polymerizing the sulfur-containing alkanoic acid to produce a sulfur-containing polymer.

In some embodiments, the sulfur-containing alkanoic acid may be isolated, and optionally purified, before undergoing condensation polymerization to produce the sulfur-containing polymer. In other embodiments, the sulfur-containing alkanoic acid is neither isolated nor purified before further use.

In some variations, the beta-lactone may be a compound of formula (1) as described herein. Any of the variations of the compound of formula (1) as described herein, e.g., with respect to the production of sulfur-containing polymers using dithionite compounds may be employed for production of sulfur-containing polymers using hydrogen sulfide or a salt thereof.

In other variations, the resulting sulfur-containing polymer comprises repeating units of formula In certain variations, for example, when the compound of formula (1) is the resulting sulfur-containing polymer comprises repeating units of formula Production of Sulfur-Containing Polymers Using Thiol Compounds In some aspects, provided is a method of producing sulfur-containing polymers from beta-lactones and thiol compounds. In some embodiments, the method comprises: combining a beta-lactone with a thiol compound to produce a sulfur-containing alkanoic acid; and polymerizing the sulfur-containing alkanoic acid to produce a sulfur-containing polymer (e.g., a polythioester).

Thiol Compounds

In some embodiments, the thiol compound is an organosulfur compound comprising at least one thiol functional group. In certain embodiments, the thiol compound comprises two or more thiol functional groups.

In some embodiments, the thiol compound comprises one thiol functional group. In some embodiments, the thiol compound is a compound of formula (B):

$$R^v\text{—SH} \quad (B),$$

wherein $R^v$ is alkyl, cycloalkyl, aryl or heteroaryl, each of which is optionally substituted with one or more substituents selected from the group consisting of —OH and —COOH.

In some variations, $R^v$ is unsubstituted -alkyl-. In other variations, $R^v$ is -alkyl-substituted with one or more substituents selected from the group consisting of —OH and —COOH. In some variations of the foregoing, $R^v$ is —$C_{1-20}$ alkyl-, —$C_{1-15}$ alkyl-, —$C_{1-10}$ alkyl-, —$C_{1-6}$ alkyl-, or —$C_{1-4}$ alkyl-.

In some variations, $R^v$ is unsubstituted -aryl-. In other variations, $R^v$ is -aryl-substituted with one or more substituents selected from the group consisting of —OH and —COOH.

Figure 2A:
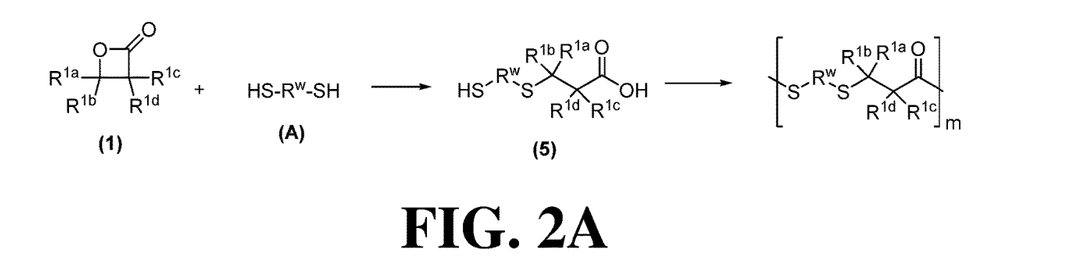
FIGS. 2A and 2B depict exemplary reaction schemes to produce sulfur-containing polymers from beta-lactones using a dithiol compound.

In some embodiments, the compound of formula (B) is:

In other embodiments, the thiol compound comprises two thiol functional groups. For example, as depicted in FIG. 2A, the thiol compound is a compound of formula (A):

$$HS\text{—}R^w\text{—}SH \quad (A),$$

wherein $R^w$ is -alkyl-, -cycloalkyl-, -aryl-, -heteroaryl-, -ether-, or -arylalkyl-.

In some variations, $R^w$ is -alkyl-. In certain variations, R is —$C_{1-20}$ alkyl-, —$C_{1-15}$ alkyl-, —$C_{1-10}$ alkyl-, —$C_{1-6}$ alkyl-, or —$C_{1-4}$ alkyl-.

In other variations, $R^w$ is -aryl-. In certain variations, $R^w$ is -phenyl- or -biphenyl-.

In yet other variations, $R^w$ is -ether-. In certain variations, $R^w$ is wherein k is an integer greater than or equal to 1. In one variation, k is 1 to 10; 1 to 6; or 1 to 4.

In some variations of the foregoing, the -alkyl-, -cycloalkyl-, -aryl-, -heteroaryl-, -ether-, and -arylalkyl- is unsubstituted.

In some embodiments, the compound of formula (A) is:

In variations where a dithiol compound, such as a compound of formula (A) is used, with reference to FIG. 2A, an exemplary method to produce a sulfur-containing polymer from beta-lactone is provided.

In FIG. 2A, the beta-lactone is a compound of formula (1):

wherein each $R^{1a}$, $R^{1b}$, $R^{1c}$ and $R^{1d}$ is independently H or alkyl. The compound of formula (1) is combined with a thiol of formula (A):

(A), wherein $R^w$ is -alkyl-, -cycloalkyl-, -aryl-, -heteroaryl-, -ether-, or -arylalkyl-. The combining of the compound of formula (1) with the thiol of formula (A) produces a compound of formula (5):

(5)

wherein $R^{1a}$, $R^{1b}$, $R^{1c}$ and $R^{1d}$ are as defined above for formula (1), and $R^w$ is as defined above for formula (A).

In some embodiments of the exemplary method depicted in FIG. 2A, the compound of formula (5) may be isolated, and optionally purified, before undergoing condensation polymerization to produce the sulfur-containing polymer. In other embodiments, the compound of formula (5) is neither isolated nor purified before further use.

With reference again to FIG. 2A, the compound of formula (5) is polymerized to produce the sulfur-containing polymer.

Figure 2B:
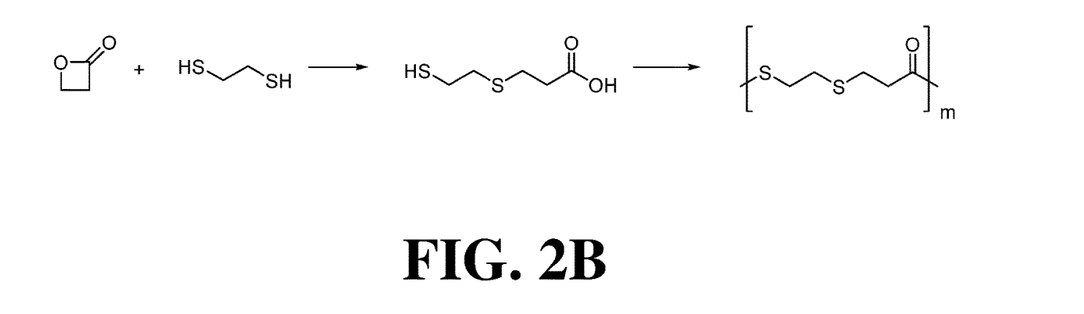

In some variations, the sulfur-containing polymer comprises repeating units of formula:

wherein $R^{1a}$, $R^{1b}$, $R^{1c}$, $R^{1d}$ and $R^w$ are as defined above for formula (5). For example, with reference to FIG. 2B, when beta-propiolactone is used, the compound of formula (5) is 3-((2-mercaptoethyl)thio)propanoic acid, which can then be polymerized to produce a polymer comprising repeating units having the structure:

The reagents and products described in the exemplary method in FIG. 2A are described in further detail below.

Compound of Formula (1)

Any of the variations of the compound of formula (1) as described herein, e.g., with respect to the production of sulfur-containing polymers using dithionite compounds may be employed for production of sulfur-containing polymers using thiol compounds.

Compound of Formula (5)

In some embodiments, the compound of formula (5) is:

(5)

wherein:
each $R^{1a}$, $R^{1b}$, $R^{1c}$ and $R^{1d}$ is independently H or alkyl, and
$R^w$ is -alkyl-, -cycloalkyl-, -aryl-, -heteroaryl-, -ether-, or -arylalkyl-.

In one variation, $R^{1a}$ is H. In other variations, $R^{1a}$ is alkyl. In certain variations, $R^{1a}$ is $C_{1-6}$ alkyl. In another variation, $R^{1a}$ is methyl, ethyl or propyl. In one variation, $R^{1b}$ is H. In other variations, $R^{1b}$ is alkyl. In certain variations, $R^{1b}$ is $C_{1-6}$ alkyl. In another variation, $R^{1b}$ is methyl, ethyl or propyl. In one variation, $R^{1c}$ is H. In other variations, $R^{1c}$ is alkyl. In certain variations, $R^{1c}$ is $C_{1-6}$ alkyl. In another variation, $R^{1c}$ is methyl, ethyl or propyl. In one variation, $R^{1d}$ is H. In other variations, $R^{1d}$ is alkyl. In certain variations, $R^{1d}$ is $C_{1-6}$ alkyl. In another variation, $R^{1d}$ is methyl, ethyl or propyl.

In one variation, $R^w$ is -alkyl-. In certain variations, $R^w$ is $—C_{1-20}$ alkyl-, $—C_{1-15}$ alkyl-, $—C_{1-10}$ alkyl-, $—C_{1-6}$ alkyl-, or $—C_{1-4}$ alkyl-. In other variations, $R^w$ is -aryl-. In certain variations, $R^w$ is -phenyl- or -biphenyl-. In yet other variations, $R^w$ is -ether-. In certain variations, $R^w$ is

, wherein k is an integer greater than or equal to 1. In one variation, k is 1 to 10; 1 to 6; or 1 to 4. In some variations of the foregoing, the -alkyl-, -cycloalkyl-, -aryl-, -heteroaryl-, -ether-, and -arylalkyl- is unsubstituted.

When the compound of formula (5) is derived from the compound of formula (1) and the thiol of formula (A), as depicted in FIG. 2A, $R^{1a}$, $R^{1b}$, $R^{1c}$ and $R^{1d}$ are as defined above for formula (1), and $R^w$ is as defined above for formula (A). For example, with reference to FIG. 2B, when the compound of formula (1) is beta-propiolactone and the thiol compound is ethane-1,2-dithiol, the compound of formula (5) produced is (also referred to as 3-((2-mercaptoethyl)thio)propanoic acid).

Polymerization

Any suitable conditions to convert the compound of formula (5) to the sulfur-containing polymer may be employed. For example, in some variations, the conversion is performed at a temperature between 180° C. and 240° C.

In other aspects, provided is a method of producing sulfur-containing polymers, comprising polymerizing a sulfur-containing alkanoic acid to produce the sulfur-containing polymer. Any of the sulfur-containing alkanoic acids, including the compound of formula (5), described above may be used to produce the sulfur-containing polymers.

Production of Phosphorus-Containing Polymers Using Phosphanediamine and Phosphanetriamine Compounds In other aspects, provided is a method of producing phosphorus-containing polymers from beta-lactones. In some embodiments, the method comprises: combining a beta-lactone with a diol compound to produce an alkanoate compound having two terminal hydroxy groups; and combining the alkanoate compound with a phosphanediamine or phosphanetriamine compound to produce a phosphorus-containing polyester.

Figure 3A:
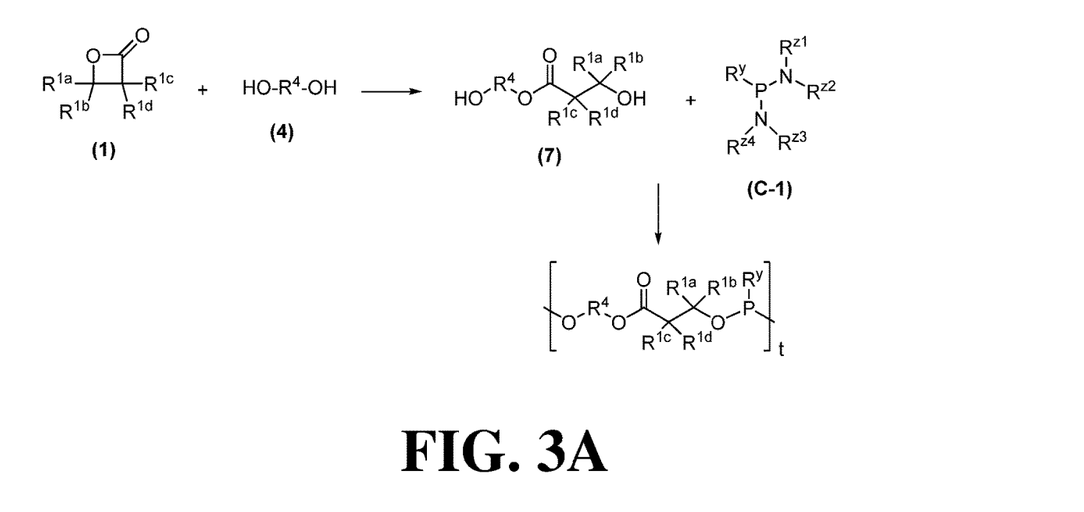
FIGS. 3A and 3B depict exemplary reaction schemes to produce phosphorus-containing polymers from beta-lactones using a diol compound.

With reference to FIG. 3A, an exemplary method to produce a phosphorus-containing polyester is provided. In FIG. 1A, the beta-lactone is a compound of formula (1):

(1)

wherein each $R^{1a}$, $R^{1b}$, $R^{1c}$ and $R^{1d}$ is independently H or alkyl. The compound of formula (1) is combined with a diol of formula (4):

wherein $R^4$ is -alkyl-, -cycloalkyl-, -aryl-, -heteroaryl-, -ether-, or -arylalkyl-. The combining of the compound of formula (1) with the diol of formula (4) produces a compound of formula (7):

wherein $R^{1a}$, $R^{1b}$, $R^{1c}$ and $R^{1d}$ are as defined above for formula (1), and $R^4$ is as defined above for formula (4).

In some embodiments of the exemplary method depicted in FIG. 3A, the compound of formula (7) may be isolated, and optionally purified, before undergoing condensation polymerization to produce the phosphorus-containing polymer. In other embodiments, the compound of formula (7) is neither isolated nor purified before further use.

With reference again to FIG. 3A, the compound of formula (7) is then combined with a phosphanediamine of formula (C-1):

(C-1)

wherein:
each $R^{z1}$, $R^{z2}$, $R^{z3}$ and $R^{z4}$ is independently alkyl; and $R^y$ is alkyl or $OR^{y1}$, wherein $R^{y1}$ is alkyl.

In other variations, the compound of formula (7) may be combined with a phosphanetriamine, as described in further detail herein.

The compound of formula (7) and the phosphanediamine compound are combined under conditions suitable for polymerization to produce the phosphorus-containing polyester.

Figure 3B:
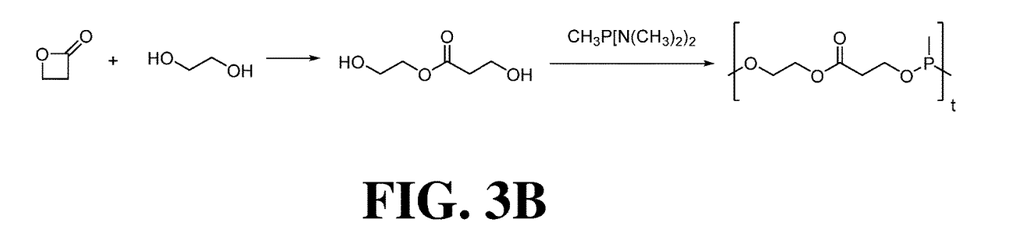

In some variations, the phosphorus-containing polyester comprises repeating units of formula:

wherein $R^{1a}$, $R^{1b}$, $R^{1c}$, $R^{1d}$ and $R^4$ are as defined above for formula (7), and $R^y$ is as defined above for formula (C-1). For example, with reference to FIG. 3B, when beta-propiolactone is used and the diol of formula (4) is ethane-1,2-diol (also known in the art as ethylene glycol), the compound of formula (7) is 2-hydroxyethyl 3-hydroxypropanoate, which can then be combined with a phosphanediamine compound such as to produce a polymer comprising repeating units having the structure:

wherein $R^{1a}$, $R^{1b}$, $R^{1c}$, $R^{1d}$ and $R^4$ are as defined above for formula (7), and $R^y$ is as defined above for formula (C-1).

The reagents and products described in the exemplary method in FIG. 3A are described in further detail below.

Compound of Formula (1)

Any of the variations of the compound of formula (1) as described herein, e.g., with respect to the production of sulfur-containing polymers using dithionite compounds may be employed for production of phosphorus-containing polyesters.

Diol Compounds

Any of the variations of the diol of formula (4) as described herein, e.g., with respect to the production of sulfur-containing polymers using dithionite compounds may be employed for production of phosphorus-containing polyesters.

Compound of Formula (7)

In some embodiments, the compound of formula (7) is:

wherein:

each $R^{1a}$, $R^{1b}$, $R^{1c}$ and $R^{1d}$ is independently H or alkyl, and $R^4$ is -alkyl-, -cycloalkyl-, -aryl-, -heteroaryl-, -ether-, or -arylalkyl-.

In one variation, $R^{1a}$ is H. In other variations, $R^{1a}$ is alkyl. In certain variations, $R^{1a}$ is $C_{1-6}$ alkyl. In another variation, $R^{1a}$ is methyl, ethyl or propyl. In one variation, $R^{1b}$ is H. In other variations, $R^{1b}$ is alkyl. In certain variations, $R^{1b}$ is $C_{1-6}$ alkyl. In another variation, $R^{1b}$ is methyl, ethyl or propyl. In one variation, $R^{1c}$ is H. In other variations, $R^{1c}$ is alkyl. In certain variations, $R^{1c}$ is $C_{1-6}$ alkyl. In another variation, $R^{1c}$ is methyl, ethyl or propyl. In one variation, $R^{1d}$ is H. In other variations, $R^{1d}$ is alkyl. In certain variations, $R^{1d}$ is $C_{1-6}$ alkyl. In another variation, $R^{1d}$ is methyl, ethyl or propyl.

In some variations, $R^4$ is -alkyl-. In certain variations, $R^4$ is —$C_{1-6}$ alkyl-. In one variation, $R^4$ is methyl. In another variation, $R^4$ is ethyl.

When the compound of formula (7) is derived from the compound of formula (1) and the diol of formula (4), as depicted in FIG. 3A, $R^{1a}$, $R^{1b}$, $R^{1c}$ and $R^{1d}$ is as defined above for formula (1), and $R^4$ is as defined above for formula (4). For example, with reference to FIG. 3B, when the compound of formula (1) is beta-propiolactone and the diol compound is ethylene glycol, the compound of formula (7) is 2-hydroxyethyl 3-hydroxypropanoate.

Phosphanediamine or Phosphanetriamine Compounds

In some embodiments, a phosphanediamine compound is used to produce the phosphorus-containing compound. In certain embodiments, the phosphanediamine compound is a compound of formula (C-1):

(C-1)

wherein:

each $R^{z1}$, $R^{z2}$, $R^{z3}$ and $R^{z4}$ is independently alkyl; and $R^y$ is alkyl or $OR^{y1}$, wherein $R^{y1}$ is alkyl.

In one variation, $R^{z1}$ is $C_{1-6}$ alkyl. In another variation, $R^{z1}$ is methyl, ethyl or propyl. In one variation, $R^{z2}$ is $C_{1-6}$ alkyl. In another variation, $R^{z2}$ is methyl, ethyl or propyl. In one variation, $R^{z3}$ is $C_{1-6}$ alkyl. In another variation, $R^{z3}$ is methyl, ethyl or propyl. In other variations, $R^{z4}$ is $C_{1-6}$ alkyl. In another variation, $R^{z4}$ is methyl, ethyl or propyl.

In other variations, $R^y$ is alkyl. In one variation, $R^y$ is $C_{1-6}$ alkyl. In another variation, $R^y$ is methyl, ethyl or propyl.

In yet other variations, $R^y$ is $OR^{y1}$, wherein $R^{y1}$ is alkyl. In certain variations, $R^{y1}$ is $C_{1-6}$ alkyl. In another variation, $R^{y1}$ is methyl, ethyl or propyl.

It should generally be understood that any description of $R^{z1}$, $R^{z2}$, $R^{z3}$, $R^{z4}$ and $R^y$ described herein may be combined the same as if each and every combination were individually listed. For example, in one embodiment, the phosphanediamine compound is in which $R^{z1}$, $R^{z2}$, $R^{z3}$, $R^{z4}$ and $R^y$ are all methyl. In another embodiments, the phosphanediamine compound is in which $R^{z1}$, $R^{z2}$, $R^{z3}$ and $R^{z4}$ are all ethyl, and $R^y$ is $OR^{y1}$, wherein $R^{y1}$ is butyl.

In other embodiments, a phosphanetriamine is used to produce the phosphorus-containing compound. In certain embodiments, the phosphanetriamine is a compound of formula (C-2):

(C-2)

wherein each $R^{z1}$, $R^{z2}$, $R^{z3}$, $R^{z4}$, $R^{z5}$ and $R^{z6}$ is independently alkyl.

In one variation, $R^{z1}$ is $C_{1-6}$ alkyl. In another variation, $R^{z1}$ is methyl, ethyl or propyl. In one variation, $R^{z2}$ is $C_{1-6}$ alkyl. In another variation, $R^{z2}$ is methyl, ethyl or propyl. In one variation, $R^{z3}$ is $C_{1-6}$ alkyl. In another variation, $R^{z3}$ is methyl, ethyl or propyl. In other variations, $R^{z4}$ is $C_{1-6}$ alkyl. In another variation, $R^{z4}$ is methyl, ethyl or propyl. In one variation, $R^{z5}$ is $C_{1-6}$ alkyl. In another variation, $R^{z5}$ is methyl, ethyl or propyl. In other variations, $R^{z6}$ is $C_{1-6}$ alkyl. In another variation, $R^{z6}$ is methyl, ethyl or propyl.

It should generally be understood that any description of $R^{z1}$, $R^{z2}$, $R^{z3}$, $R^{z4}$, $R^{z5}$ and $R^{z6}$ described herein may be combined the same as if each and every combination were individually listed. For example, in one embodiment, the phosphanetriamine compound is in which $R^{z1}$, $R^{z2}$, $R^{z3}$, $R^{z4}$, $R^{z5}$ and $R^{z6}$ are all ethyl.

The phosphanediamine and phosphanetriamine compounds may be obtained from any commercially available sources or produced according to any methods known in the art.

Polymerization

Any suitable conditions to convert the compound of formula (7) to the phosphorus-containing polymer may be employed.

In other aspects, provided is a method of producing phosphorus-containing polymers, comprising combining an alkanoate compound having two terminal hydroxy groups with a phosphanediamine or phosphanetriamine compound to produce a polymer, wherein the polymer is a phosphorus-containing polyester. Any of the alkanoate compounds, including the compound of formula (7), and the phosphanediamine or phosphanetriamine compounds, including the compounds of formulae (C-1) and (C-2), may be used to produce the phosphorus-containing polymers.

Sulfur-Containing Polymers

In some aspects, provided are sulfur-containing polymers comprising repeating sulfonyl-dialkanoic acid moieties. In some embodiments, the sulfur-containing polymer comprises repeating units of formula:

wherein:
each $R^{1a}$, $R^{1b}$, $R^{1c}$ and $R^{1d}$ is independently H or alkyl; and $R^4$ is -alkyl-, -cycloalkyl-, -aryl-, -heteroaryl-, -ether-, or -arylalkyl-.

In some variations, such sulfur-containing polymer is produced from the methods described herein. For example, when the sulfur-containing polymer is produced from the compound of formula (3) and the diol of formula (4) as described herein, $R^{1a}$, $R^{1b}$, $R^{1c}$ and $R^{1d}$ are as defined for formula (3), and $R^4$ is defined for formula (4).

In other aspects, the sulfur-containing polymer comprises repeating units of formula:

wherein:
each $R^{1a}$, $R^{1b}$, $R^{1c}$ and $R^{1d}$ is independently H or alkyl; and $R^w$ is -alkyl-, -cycloalkyl-, -aryl-, -heteroaryl-, -ether-, or -arylalkyl-.

In some variations, such sulfur-containing polymer is produced from the methods described herein. For example, when the sulfur-containing polymer is produced from the compound of formula (5) as described herein, $R^{1a}$, $R^{1b}$, $R^{1c}$, $R^{1d}$ and $R^w$ are as defined for formula (5).

In some embodiments, provided is a sulfur-containing polymer having a biocontent of at least 10%, at least 20%, at least 30%, at least 40%, at least 50%, at least 60%, at least 70%, at least 80%, at least 90%, at least 95% or about 100%.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−10%.

Phosphorus-Containing Polymers

In some aspects, provided are phosphorus-containing polyesters. In some embodiments, the phosphorus-containing polymer comprises repeating units of formula:

wherein:
each $R^{1a}$, $R^{1b}$, $R^{1c}$ and $R^{1d}$ is independently H or alkyl;
$R^4$ is -alkyl-, -cycloalkyl-, -aryl-, -heteroaryl-, -ether-, or -arylalkyl-; and
$R^y$ is alkyl or $OR^{y1}$, wherein $R^{y1}$ is alkyl.

In some variations, the phosphorus-containing polymer is produced from the methods described herein. For example, when the phosphorus-containing polymer is produced from the compound of formula (7) and the phosphanediamine of formula (C-1) as described herein, $R^{1a}$, $R^{1b}$, $R^{1c}$, $R^{1d}$ and $R^4$ are as defined for formula (7), and $R^y$ is as defined for formula (C-1).

In some embodiments, provided is a sulfur-containing polymer having a biocontent of at least 10%, at least 20%, at least 30%, at least 40%, at least 50%, at least 60%, at least 70%, at least 80%, at least 90%, at least 95% or about 100%.

Compositions

In some aspects, provided is a composition comprising a sulfonyl-dialkanoic acid; and a diol compound. In some embodiments provided is a composition comprising:
a compound of formula (3) is wherein each $R^{1a}$, $R^{1b}$, $R^{1c}$ and $R^{1d}$ is independently H or alkyl; and a compound of formula (4) is HO—R⁴—OH, wherein R⁴ is -alkyl-, -cycloalkyl-, -aryl-, -heteroaryl-, -ether-, or -arylalkyl-.

In some variations of the foregoing, the composition further comprises a sulfur-containing polymer comprising repeating sulfonyl-dialkanoic acid moieties. For example, in one variation, the composition further comprises: a polymer comprising repeating units of formula wherein $R^{1a}$, $R^{1b}$, $R^{1c}$ and $R^{1d}$ are as defined above for formula (3), and $R^4$ is defined above for formula (4).

In other aspects, provided is a composition comprising a sulfur-containing alkanoic acid; and a sulfur-containing polymer. In some embodiments, provided is a composition comprising:
a compound of formula (5) is wherein:
each $R^{1a}$, $R^{1b}$, $R^{1c}$ and $R^{1d}$ is independently H or alkyl, and
$R^w$ is -alkyl-, -cycloalkyl-, -aryl-, -heteroaryl-, -ether-, or -arylalkyl-; and
a polymer comprising repeating units of formula wherein $R^{1a}$, $R^{1b}$, $R^{1c}$, $R^{1d}$ and $R^w$ are as defined above for formula (5).

In yet other aspects, provided is a composition comprising an alkanoate compound having two terminal hydroxy groups; and a phosphanediamine or phosphanetriamine compound. In some embodiments, provided is a composition comprising:
a compound of formula (7) is wherein:
each $R^{1a}$, $R^{1b}$, $R^{1c}$ and $R^{1d}$ is independently H or alkyl, and
$R^4$ is -alkyl-, -cycloalkyl-, -aryl-, -heteroaryl-, -ether-, or -arylalkyl-; and a compound of formula (C-1):

wherein:
each $R^{z1}$, $R^{z2}$, $R^{z3}$ and $R^{z4}$ is independently alkyl, and $R^y$ is alkyl or $OR^{y1}$, wherein $R^{y1}$ is alkyl, or
a compound of formula (C-2):

(C-2)

wherein each $R^{z1}$, $R^{z2}$, $R^{z3}$, $R^{z4}$, $R^{z5}$ and $R^6$ is independently alkyl.

In some variations of the foregoing when a compound of formula (C-1) is used, the composition further comprises:
a polymer comprising repeating units of formula wherein $R^{1a}$, $R^{1b}$, $R^{1c}$, $R^{1d}$ and $R^4$ are as defined above for formula (7), and $R^y$ is as defined above for formula (C-1).

What is claimed is:

1. A method, comprising:
combining a beta-lactone with a diol compound to produce an alkanoate compound having two terminal hydroxy groups; and
combining the alkanoate compound with a phosphanediamine compound or a phosphanetriamine compound to produce a phosphorus-containing polyester.

2. The method of claim 1, wherein the beta-lactone is beta-propiolactone, beta-butyrolactone, or beta-valerolactone, and wherein the diol is ethylene glycol.

3. A method according to claim 1, wherein the beta-lactone corresponds to formula (1)

wherein the diol corresponds to formula (4) HO—$R^4$—OH, wherein $R^4$ is -alkyl-, -cycloalkyl-, -aryl-, -heteroaryl-, -ether-, or -arylalkyl-; and wherein the alkanoate compound having two terminal hydroxy groups corresponds to formula (7)

wherein $R^{1a}$, $R^{1b}$, $R^{1c}$, and $R^{1d}$ is as defined for formula (1), and wherein $R^4$ is as defined above for formula (4);

wherein the phosphanediamine compound corresponds to the formula (C-1)

and wherein the phosphanetriamine compound is a compound of formula (C-2)

wherein $R^y$ is alkyl or $OR^{y1}$, and wherein $R^{y1}$ is alkyl; and wherein the polymer comprises repeating units of formula wherein each $R^{1a}$, $R^{1b}$, $R^{1c}$ and $R^{1d}$ is independently H or alkyl, $R^4$ is independently in each occurrence -alkyl-, -cycloalkyl-, -aryl-, -heteroaryl-, -ether-, or -arylalkyl-, each $R^{z1}$, $R^{z2}$, $R^{z3}$, $R^{z4}$, $R^{z5}$ and $R^{z6}$ is independently in each occurrence alkyl, $R^y$ is independently in each occurrence alkyl or —$OR^{y1}$; and $R^{y1}$ is alkyl.

4. The method of claim 3, wherein $R^{1a}$ is H or alkyl, $R^{1b}$, $R^{1c}$, and $R^{1d}$ are all H, and $R^4$ is -alkyl.

5. A polymer produced according to the method of claim 1.

* * * * *